(12) United States Patent
Cloutier et al.

(10) Patent No.: US 9,389,023 B2
(45) Date of Patent: Jul. 12, 2016

(54) WOUND HEAT EXCHANGER

(71) Applicant: Medtronic, Inc., Minneapolis, MN (US)

(72) Inventors: Patrick Cloutier, Andover, MN (US);
Robert Olsen, Plymouth, MN (US);
Stephen Roller, Minneapolis, MN (US);
Chris Plott, St. Paul, MN (US); Al McLevish, Apple Valley, MN (US);
Ming Li, Roseville, MN (US); Michael Laxen, Minneapolis, MN (US); John Knoll, Brooklyn Park, MN (US);
Gregory Hake, Otsego, MN (US)

(73) Assignee: Medtronic, Inc., Minneapolis, MN (US)

( * ) Notice: Subject to any disclaimer, the term of this patent is extended or adjusted under 35 U.S.C. 154(b) by 156 days.

(21) Appl. No.: 14/063,182

(22) Filed: Oct. 25, 2013

(65) Prior Publication Data

US 2014/0048234 A1    Feb. 20, 2014

Related U.S. Application Data

(62) Division of application No. 13/015,398, filed on Jan. 27, 2011, now Pat. No. 8,579,845.

(51) Int. Cl.
*A61M 1/16* (2006.01)
*F28D 15/04* (2006.01)
*A61M 1/36* (2006.01)
(Continued)

(52) U.S. Cl.
CPC ........... *F28D 15/046* (2013.01); *A61M 1/1698* (2013.01); *A61M 1/367* (2013.01); *A61M 1/369* (2013.01); *B01D 63/025* (2013.01); *B01D 2313/38* (2013.01); *B29C 53/083* (2013.01);
(Continued)

(58) Field of Classification Search
CPC . A61M 1/1629; A61M 1/1698; A61M 1/367; A61M 1/369; B01D 2313/38; B01D 63/025; B29C 53/083; B29L 2031/18; F28D 15/046; Y10T 29/49353
See application file for complete search history.

(56) References Cited

U.S. PATENT DOCUMENTS

| | | |
|---|---|---|
| 3,422,008 A | 1/1969 | Melain |
| 3,755,034 A | 8/1973 | Mahon et al. |

(Continued)

FOREIGN PATENT DOCUMENTS

| | | |
|---|---|---|
| WO | WO94/26327 | 11/1994 |
| WO | WO97/25080 | 7/1997 |

OTHER PUBLICATIONS 2013-551263, Japanese Office Action, mailed Nov. 30, 2015.

*Primary Examiner* — Tatyana Zalukaeva
*Assistant Examiner* — Benjamin Klein

(57) ABSTRACT

A capillary tube bundle sub-assembly for use in an extracorporeal heat exchanger includes a continuous capillary tubing wound about a core to define a plurality of capillary layers each including a plurality of capillary segments. The capillary segments each define opposing terminal ends adjacent opposing ends of the core. The capillary segments of each layer are circumferentially aligned relative to an axis of the core, with each successive layer being radially outward of an immediately preceding layer. The capillary segments are non-parallel with the axis, spiraling partially about the axis in extension between the opposing terminal ends. Each capillary segment forms less than one complete revolution (i.e., winds less than 360°). The segments within each layer are substantially parallel with one another; however, an orientation of the segments differs from layer-to-layer such as by pitch or angle.

17 Claims, 20 Drawing Sheets

(51) Int. Cl.
  *B01D 63/02*   (2006.01)
  *B29C 53/08*   (2006.01)
  *B29L 31/18*   (2006.01)

(52) U.S. Cl.
  CPC ........ *B29L 2031/18* (2013.01); *Y10T 29/49353* (2015.01)

(56) References Cited

U.S. PATENT DOCUMENTS

| | | | |
|---|---|---|---|
| 3,794,468 A * | 2/1974 | Leonard et al. ................. 422/48 |
| 4,031,012 A | 6/1977 | Gics |
| 4,572,446 A | 2/1986 | Leonard et al. |
| 4,622,206 A | 11/1986 | Torgeson |
| 4,863,600 A | 9/1989 | Leonard et al. |
| 4,940,617 A | 7/1990 | Baurmeister |
| 4,975,247 A | 12/1990 | Badolato et al. |
| 5,143,312 A | 9/1992 | Baurmeister |
| 5,299,749 A | 4/1994 | Thorogood et al. |
| 5,376,334 A | 12/1994 | Haworth et al. |
| 5,462,619 A | 10/1995 | Haworth et al. |
| 5,702,601 A | 12/1997 | Bikson et al. |
| RE36,125 E | 3/1999 | Haworth et al. |
| 5,897,729 A | 4/1999 | Bikson et al. |
| 6,273,355 B1 * | 8/2001 | Van Driel et al. .......... 242/433.3 |
| 6,503,451 B2 | 1/2003 | Ikeda et al. |
| 6,508,983 B1 | 1/2003 | McBurney et al. |
| 6,638,479 B1 | 10/2003 | Elgas et al. |
| 2010/0269342 A1 | 10/2010 | Carpenter et al. |
| 2010/0272607 A1 | 10/2010 | Carpenter |

\* cited by examiner

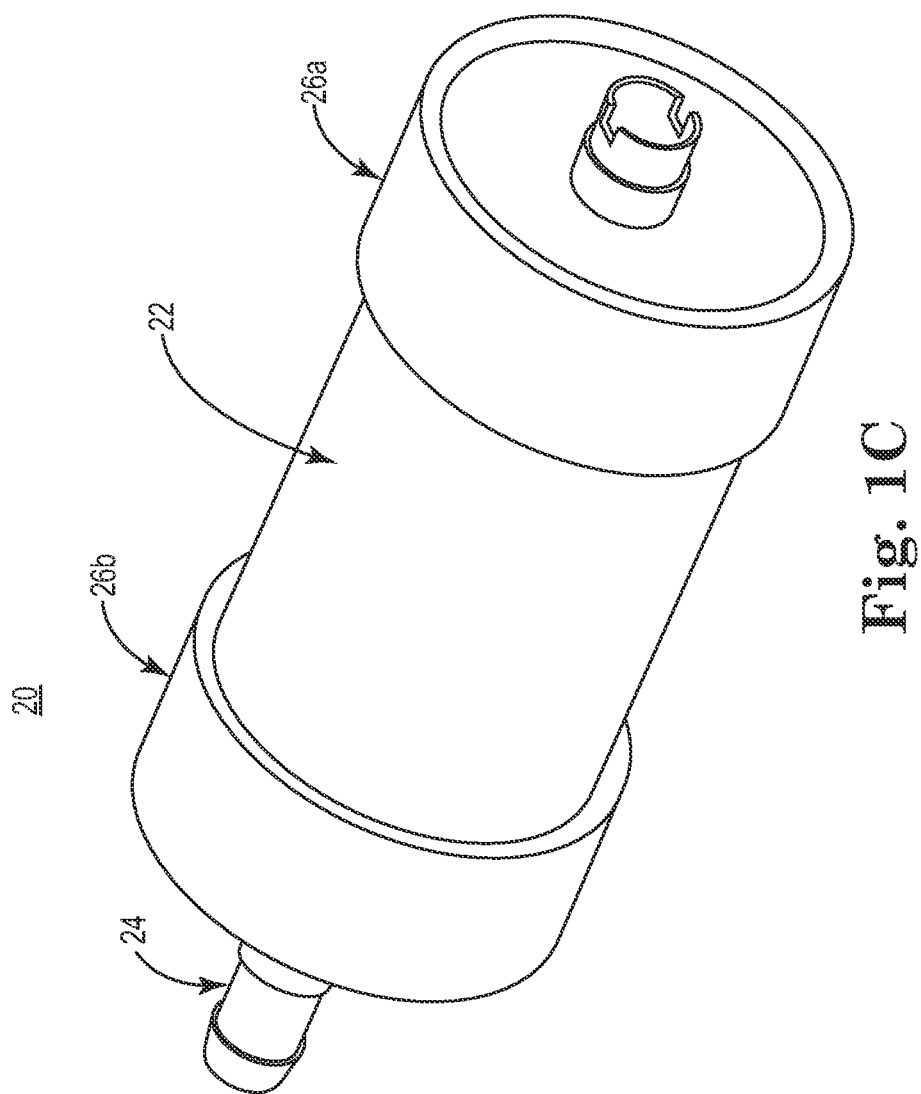

WOUND HEAT EXCHANGER

RELATED APPLICATIONS

This application is a Division of and claims the benefit of U.S. patent application Ser. No. 13/015,398 filed Jan. 27, 2011, now allowed. The disclosures of which are herein incorporated by reference in their entirety.

BACKGROUND

The present disclosure relates to capillary tubing heat exchangers. More particularly, it relates to capillary tube bundles useful in extracorporeal blood circuit heat exchangers, and related methods of manufacture.

Fluid-to-fluid heat exchangers are used in many different industries, and are typically constructed in conjunction with the intended end use. For example, a heat exchanger is an important component of an extracorporeal or cardiopulmonary bypass circuit. As a point of reference, an extracorporeal blood circuit is commonly used during cardiopulmonary bypass (i.e., a heart-lung bypass machine) to withdraw blood from the venous portion of the patient's circulation system and return the blood to the arterial portion. The extracorporeal blood circuit generally includes a venous line, a venous blood line reservoir, a blood pump, an oxygenator, a heat exchanger, an arterial line, and blood transporting tubing, ports, and connection pieces interconnecting the components. The heat exchanger regulates a temperature of the extracorporeal blood as desired. For example, the heat exchanger can be located upstream of the oxygenator and operated to cool the blood arriving from the patient prior to oxygenation; alternatively, the heat exchanger can be operated to warm the extracorporeal blood.

Regardless of the direction of heat transfer between the heat exchanger and the patient's blood, extracorporeal blood circuit heat exchangers generally consist of metal bellows and a multiplicity of metal or plastic tubes (capillary tubes); a suitable heat exchange fluid, such as water, is pumped through the tube lumens while the blood flows about the tube exteriors. The heat exchange fluid can be heated or cooled (relative to a temperature of the blood). As blood contacts the tubes, heat transfer occurs between the blood and the heat exchange fluid in an intended direction. Alternatively, blood flow can be through the tube lumens, with the heat exchange fluid flowing about the tube exteriors.

So as to have minimal impact on the circuit's prime volume, the extracorporeal heat exchanger is desirably as small as possible, while still providing high heat exchange efficiency. To meet these requirements, the capillary tubes are micro-diameter or fiber-like (e.g., outer diameter no greater than about 0.05 inch). The heat exchange fluid is fluidly isolated from blood of the extracorporeal circuit by a wall thickness of the capillaries, keeping the fluids separate but allowing the transfer of heat from one fluid to the other.

A common capillary tubing format pre-assembles a large number of the micro-diameter tubes into a mat. The capillary tubes are knitted, woven or otherwise held together with threads or stitching forming the warp of the mat. For heat exchanger applications, the capillary tube mat must be bundled together in some fashion to form a capillary tube bundle. Typically, the mat is wrapped or rolled around a core or mandrel. As the mat is continuously wound about the mandrel, the mat wraps or winds onto itself, resulting in a series of radially increasing layers. The capillary tubes of the mat are conventionally "biased" so that the tubes are not parallel with a width of the mat. Two layers of the mat with opposite bias angles can be simultaneously wound on the core to prevent the capillaries of subsequent layers from nesting in the gaps between capillary tubes of a preceding layer as the mat is wrapped onto itself.

While highly viable, capillary mat-based heat exchangers have certain drawbacks. For example, capillary tubing mats are expensive due to the complexities of the knitting or weaving process. Further, the size, bias, materials, spacing, etc., of the capillary tubes is fixed, such that possible benefits available with varying one or more of these parameters is unavailable.

Capillary tube bundles are also used in other mass transfer devices, and in particular blood oxygenators. As a point of reference, the capillary tubing employed with oxygenators is markedly different from that of heat exchangers; oxygenator capillary tubing is porous or semi-permeable, whereas heat exchanger capillary tubing is fluid impermeable. These differences affect fluid flow properties and may impact manufacturing techniques. In any event, a woven capillary tube mat akin to the above descriptions can be used to form an oxygenator capillary tube bundle. In an alternative approach, a single capillary tube, or ribbon of capillary tubes, is directly wound onto a rotating core, generating a helical wind pattern. One such oxygenator bundle winding technique is set forth in U.S. Pat. No. 4,975,247 that otherwise describes the means by which to wind an oxygenator capillary tube with specialized winding equipment. Regardless of whether such techniques are applicable to heat exchanger capillary tube bundles, the helical winding format of the '247 Patent (and other similar techniques) results in an interleaving of the capillary tubes within each layer. In many instances, this interleaving may be less than optimal for extracorporeal blood circuit heat exchanger functioning and performance.

In light of the above, a need exists for improved heat exchanger capillary tube bundle manufacturing techniques that combine low cost and direct control over production, as well as for the capillary tube bundles and heat exchangers resulting from such techniques.

SUMMARY

Some aspects of the present disclosure relate to a capillary tube bundle sub-assembly for use in an extracorporeal blood circuit heat exchanger. The capillary tube bundle sub-assembly includes a substrate core and at least one continuous capillary tubing. The core defines a cylindrical outer surface having a central longitudinal axis, a first core end, a second core end opposite the first end, and a length between the opposing core ends in a direction of the central axis. The capillary tubing is wound about the outer surface to define a plurality of layers that each include a plurality of capillary segments. The capillary segments traverse at least a majority of the core length, with each capillary segment defining a first terminal end, adjacent the first core end and a second terminal end adjacent the second core end. The capillary segments of each layer are circumferentially aligned relative to the central axis, with each successive layer being radially outward of an immediately preceding layer. An entirety of each of the capillary segments is non-parallel with the central axis, spiraling partially about the central axis in extension between the corresponding opposing terminal ends. In this regard, each capillary winds or segment wraps about the central axis by less than one complete revolution (i.e., winds less than 360°).

With so-constructed sub-assembly, the conventional capillary tube mat, and attendant cost, is eliminated, and the orientation (as well as other parameters) of the capillary segments can be varied from layer-to-layer. This feature, in turn, facilitates optimized performance of a capillary tube bundle produced from the sub-assembly when employed as part of a heat exchanger, including heat transfer rates and pressure drop. In some embodiments, the capillary segments of each individual layer are parallel with one another, but an orientation of the capillary segments differs from layer-to-layer. For example, the capillary segments of a first layer are oriented in a first pitch direction, whereas the capillary segments of an immediately adjacent second layer are oriented in an opposite pitch direction. In related embodiments, the capillary segments of the first layer are oriented at a first angle relative to the central axis, whereas the capillary segments of the immediately adjacent second layer are oriented at a different, second angle. With these and other constructions, the capillary segments of immediately adjacent layers will not nest between each other. Further, by varying a pitch or angle of the capillary segment between two (or more) layers, a desired packing fraction can be achieved, and can be selected to optimize a desired shear rate of blood flow between the layers.

Yet other aspects in accordance with principles of the present disclosure relate to an extracorporeal blood circuit apparatus for heat exchanging. The apparatus includes a housing and a capillary tube bundle. The housing defines a blood flow path and a heat exchange fluid path. The blood flow path is defined between a blood inlet and a blood outlet. The heat exchange fluid path is defined between a heat exchange inlet and a heat exchange outlet. The capillary tube bundle is disposed within the housing, and includes a core and plurality of capillary tubes disposed about an outer surface of the core. The capillary tubes define a plurality of layers, with the capillary tubes of each layer being substantially circumferential aligned. Each successive layer is radially outward of an immediately preceding layer. The tubes each have opposing, first and second open ends located adjacent corresponding ends of the core, and traverse a majority of the length of the core. In this regard, each of the tubes is non-parallel with a central axis of the core, and spirals partially about the central axis by less than 360°. An orientation (e.g., pitch direction, angle, etc.) of the tubes of a first layer differs from an orientation of the tubes of a second layer. A first band is disposed about the first open end of each of the capillary tubes, with the first open ends being fluidly open to the blood inlet or the heat exchange inlet. A second band is disposed about the second open end of each of the capillary tubes, with the second open ends being fluidly open to the corresponding blood outlet or heat exchange outlet. When assembled into an extracorporeal blood circuit, then, the apparatus operates to effectuate heat exchange with the patient's blood in a desired direction. For example, a lower temperature liquid can be pumped through the capillary tube lumens via the heat exchange fluid path; blood from the patient flows radially between the capillary tubes, with heat from the blood being thoroughly transferred to the heat exchange liquid, thereby cooling the patient's blood.

Yet other aspects in accordance with principles of the present disclosure relate to a method of making a capillary tube bundle for use in a heat exchanger of an extracorporeal blood circuit apparatus. The method includes guiding a continuous capillary tubing in a first direction along an outer cylindrical surface of a core substrate to form a first capillary segment extending from a first terminal end adjacent a first core end of the core to a second terminal end adjacent an opposing, second core end of the core. The first terminal end is circumferentially offset from the second terminal end such that an entirety of the first capillary segment is non-parallel with a central axis of the core. Further, the first capillary segment traverses less than 360° of the outer surface. The continuous capillary tubing is further guided in a second direction opposite the first direction to form a second capillary segment immediately adjacent the first capillary segment. The second capillary segment is formed to define opposing, first and second terminal ends. The so-formed first and second capillary segments combine to form a portion of a first layer of capillary segments substantially circumferentially aligned about the central axis. Finally, the continuous capillary tubing is guided in a reciprocating fashion relative to the core to form a second layer of capillary segments radially outward of the first layer. In some embodiments, a pitch direction and/or angle of the capillary segments of the first layer differs from that of the capillary segments of the second layer, in yet other embodiments, the capillary tubing is guided to form a multiplicity of circumferential layers. In other embodiments, the capillary segments are cut to form discrete, open-ended capillary tubes.

BRIEF DESCRIPTION OF THE DRAWINGS

FIG. 1C is a perspective view of the capillary tube bundle of FIG. 1A;

DETAILED DESCRIPTION

Figure 1A:
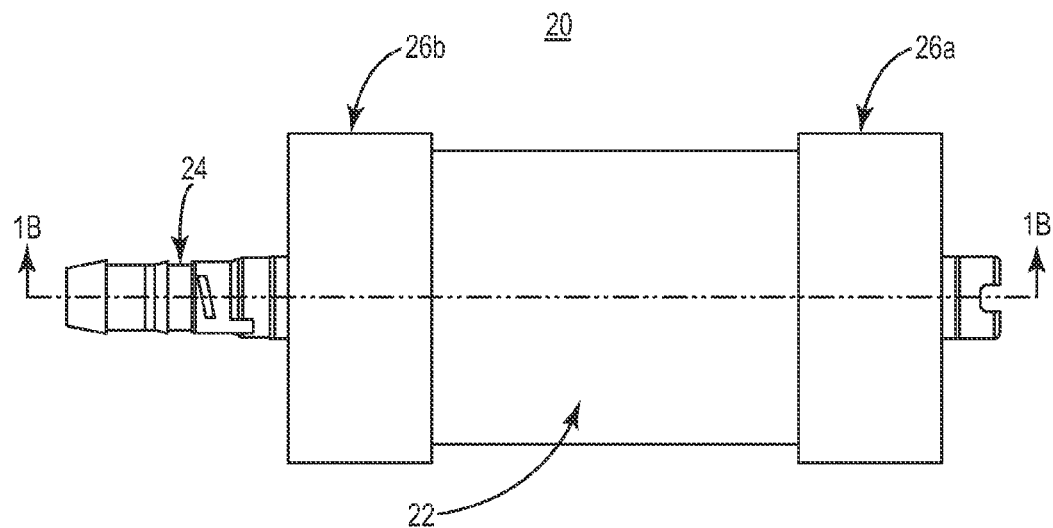
FIG. 1A is a side view of a capillary tube bundle in accordance with principles of the present disclosure.
Figure 1B:
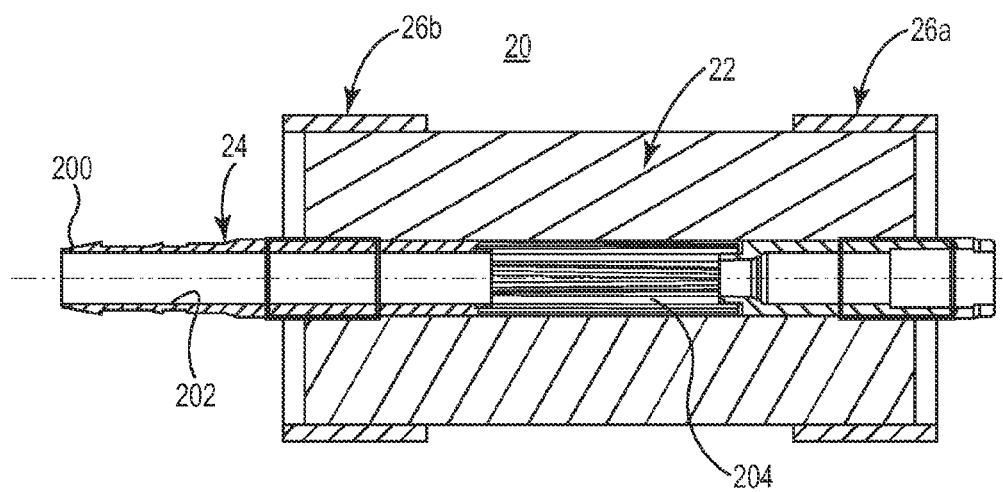
FIG. 1B is a cross-sectional view of the capillary tube bundle of FIG. 1A, taken along the line 1B-1B.

One embodiment of a capillary tube bundle 20 in accordance with principles of the present disclosure and useful as part of an extracorporeal blood circuit heat exchanger apparatus is shown in FIGS. 1A-1C. The capillary tube bundle 20 includes a plurality of micro-diameter capillary tubes or heat transfer elements (schematically illustrated in FIGS. 1A-1C) 22, a core 24, and optional bands or caps 26a, 26b. Details on the various components are provided below. In general terms, however, the capillary tubes 22 are formed about the core 24 pursuant to the methodologies described below, including initial formation of a wound capillary tube bundle sub-assembly. The bands 26a, 26b (where provided) serve to secure the capillary tubes 22 about the core 24. The capillary tube bundle 20 can be employed in various end-use applications, but is particularly useful as part of a heat exchanger or heat exchanger apparatus employed in an extracorporeal blood circuit. In some embodiments, the capillary tube bundle 20 is connected within the extracorporeal blood circuit (or other environment requiring transfer of heat between fluids) as part of a standalone heat exchanger apparatus; alternatively, the capillary tube bundles of the present disclosure can be assembled to, or formed as part of a combination device, for example serving as the heat exchanger of a combination oxygenator and heat exchanger apparatus.

Figure 2A:
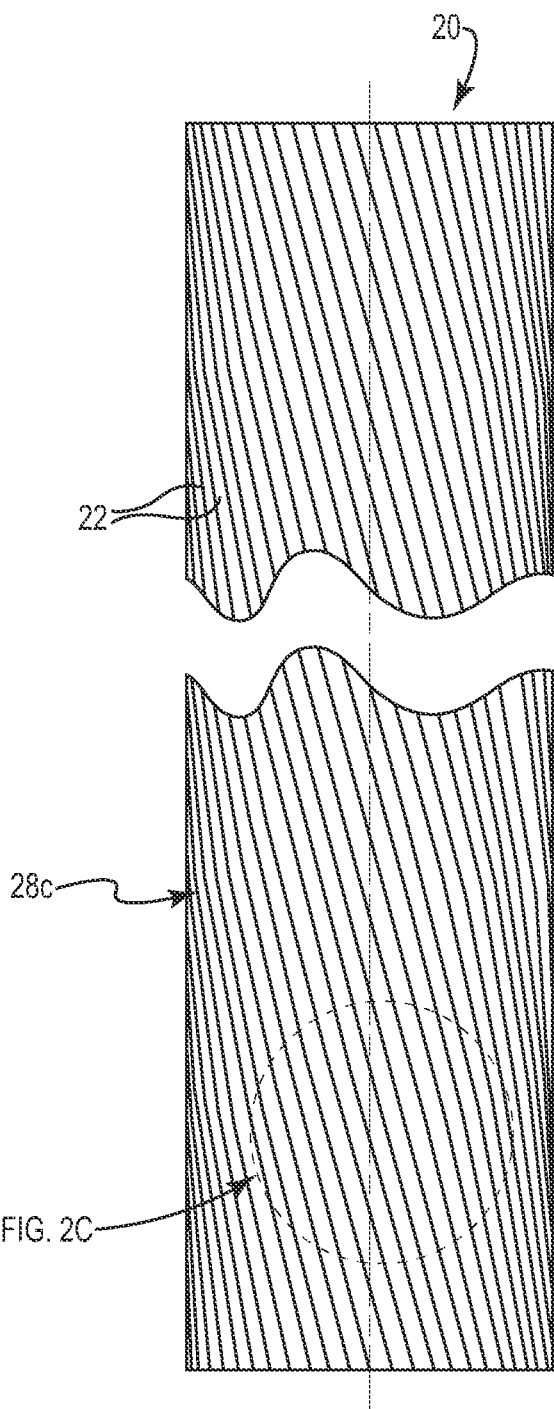
FIG. 2A is a side view of the capillary tubes provided with the bundle of FIG. 1A.
Figure 2B:
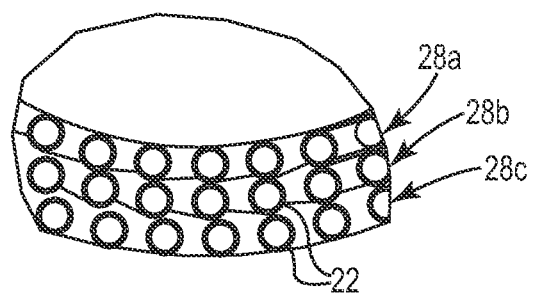
FIG. 2B is a magnified end view of a portion of the capillary tubes of FIG. 2A.
Figure 2C:
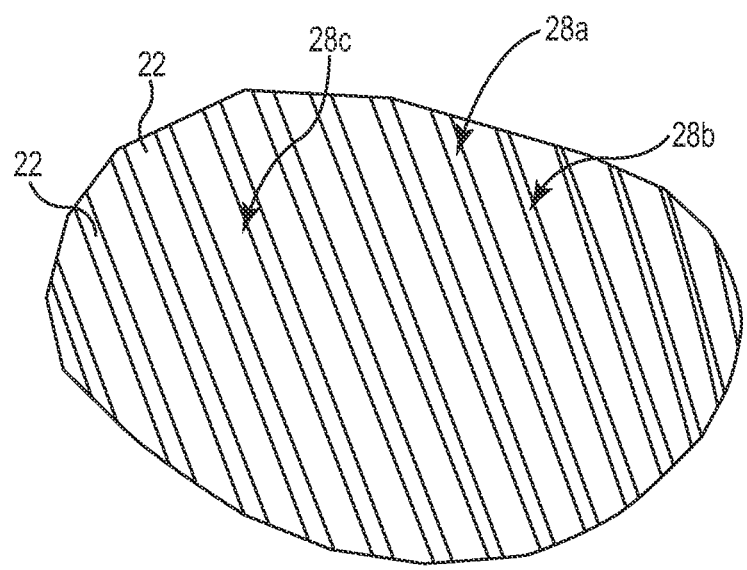
FIG. 2C is a magnified side view of a portion of the capillary tubes of FIG. 2A.

The capillary tubes 22 are micro-diameter tubes (e.g., hollow microfilaments or microfibers) as shown more clearly in FIGS. 2A-2C. The capillary tubes 22 are formed of a thermally conductive polymer or metal, for example, polyethylene terephthalate (PET) or polyurethane. The capillary tubes 22 can have an outer diameter in the range of about 0.010 inch to about 0.050 inch, and an inner diameter in the range of about 0.005 inch to about 0.030 inch, although other dimensions are also contemplated. The capillary tubes 22 are independent of one another, and are not interconnected by threads or stitching. As best shown in FIGS. 2B and 2C, the capillary tubes 22 are arranged to define a plurality of concentric layers 28a-28c, with the capillary tubes 22 of each layer 28a-28c being biased relative to the tubes 22 of an immediately adjacent layer 28a-28c.

Figure 3A:
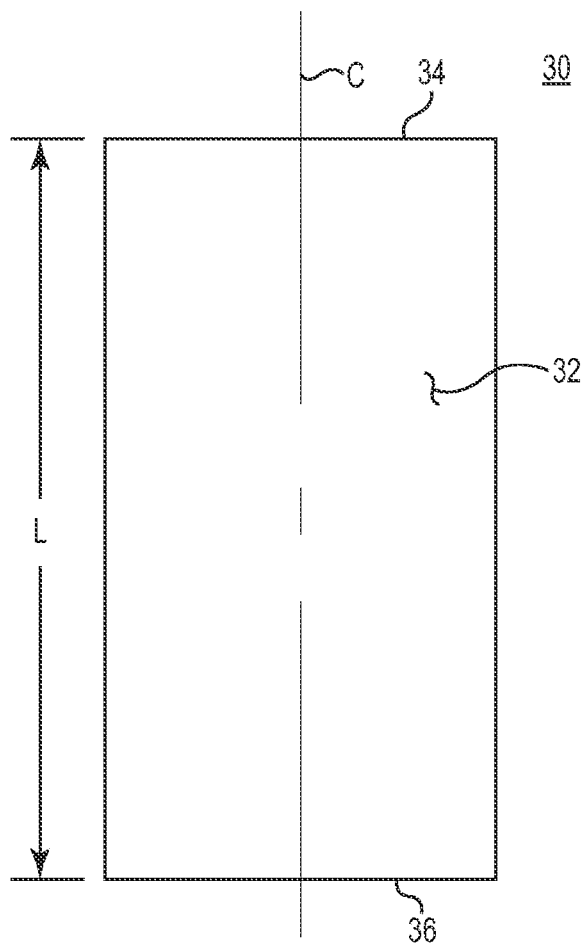
FIG. 3A is a simplified side view of a substrate winding core useful in forming a capillary tube bundle sub-assembly in accordance with principles of the present disclosure.
Figure 3B:
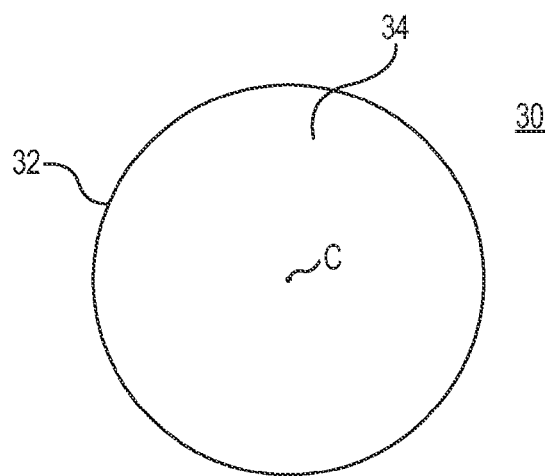
FIG. 3B is an end view of the winding core of FIG. 3A.

An explanation of various features embodied by the capillary tube bundle 20, such as the concentric layers 28a-28c of capillary tubes 22 reflected in FIGS. 2A-2C, are best understood with reference to methods of making the same in accordance with principles of the present disclosure. More particularly, aspects of the present disclosure relate to methods of forming a wound capillary tube bundle sub-assembly, as well as subsequent processing of the sub-assembly to produce the capillary tube bundle 20. With this in mind, FIGS. 3A and 3B are simplified illustrations of a winding substrate core or mandrel 30 prior to application or formation of the capillary tubes 22 (FIG. 2A). As a point of reference, the winding core 30 can be the core 24 (FIGS. 1A-1C) of the final capillary tube bundle 20 (FIGS. 1A-1C) and thus configured for use within a heat exchanger, or can be employed during manufacture of the capillary tube bundle sub-assembly and later replaced by the core 24. Regardless, the winding the core 30 has or defines a cylindrical outer surface 32, and defines opposing first and second ends 34, 36. The cylindrical shape of the core 30 defines a central longitudinal axis C, with a length L being defined between the core ends 34, 36 in a direction of the central axis C.

Figure 4A:
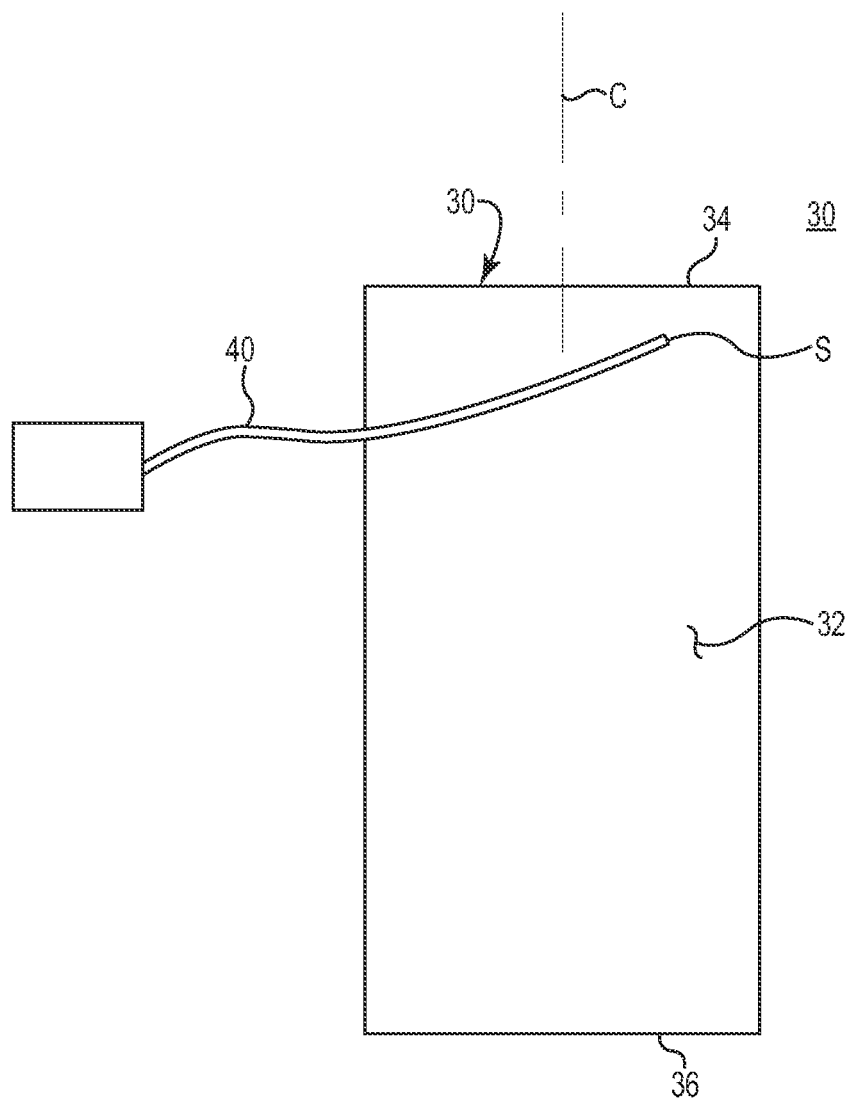
FIGS. 4A and 4B are simplified side views illustrating initial stages of winding a capillary tube to the winding core.
Figure 4B:
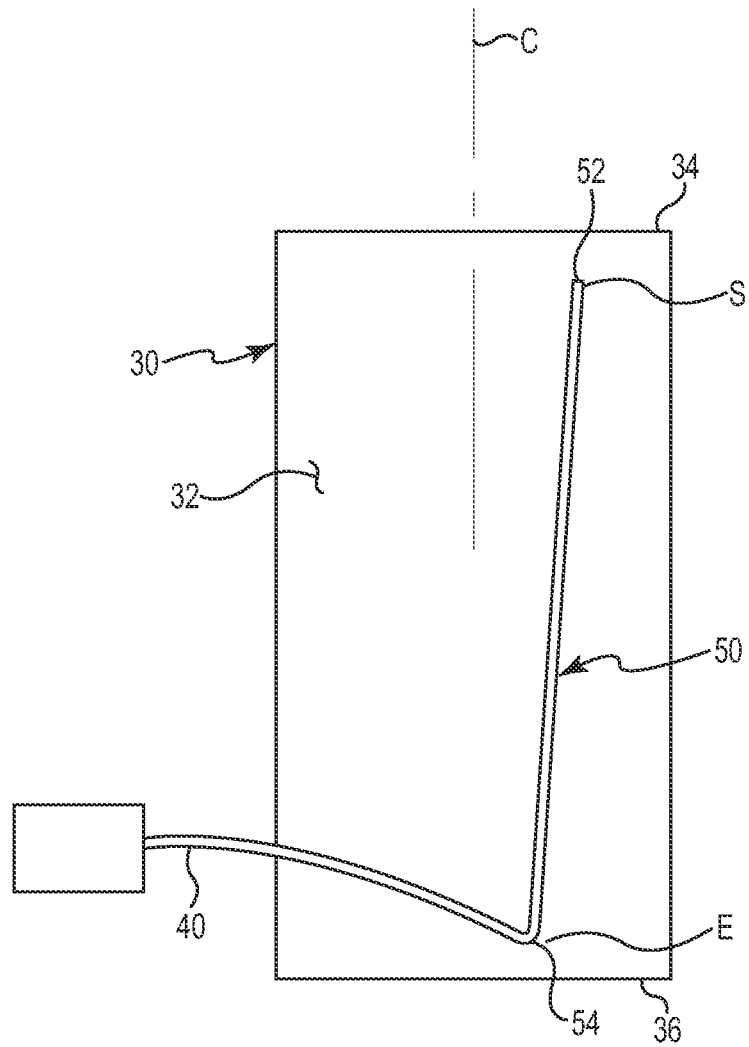

The capillary tubes 22 (FIG. 2A) are formed by initially applying (winding) one or more continuous lengths of capillary tubing 40 about the outer surface 32 as initially reflected in FIG. 4A. In some embodiments, a plurality of continuous capillary tubings 40 can be simultaneously applied to the core 30 commensurate with the foregoing descriptions; for ease of illustration, however, the following explanation provides a single one of the capillary tubing 40. The continuous capillary tubing 40 is initially secured at a starting point S to the outer surface 32 adjacent the first core end 34. For example, an adhesive, holding device (e.g., roller), friction, etc., can be employed to maintain the capillary tubing 40 at or against the outer surface 32. The capillary tubing 40 is then traversed along the outer surface 32 in a partially spiral-like manner (i.e., non-parallel with the central axis C). As shown in FIG. 4B, for example, the initial stage of winding includes extending the capillary tubing 40 from the starting point S to an end point E adjacent the second core end 36. As with the starting point S, the end point E can be slightly spaced from the second core end 36. Further, the end point E can be established in the capillary tubing 40 by various techniques, such as adhering the capillary tubing 40 to the outer surface 32, a holding device (e.g., roller), wrapping the capillary tubing 40 about a wrapping body or pin mounted to the winding core 30, friction, etc. Regardless, when traversed in this manner, the applied capillary tubing 40 now defines a first capillary segment 50 extending along the outer surface 32 (and held in tension), with the starting and end points S, E effectively defining opposing first and second terminal ends 52, 54 of the first capillary segment 50 adjacent the first and second core ends 34, 36, respectively. The first capillary segment 50 traverses at least a majority of the core length L. The opposing terminal ends 52, 54 are circumferentially offset from one another, such that the first capillary segment 50 is non-parallel with the central axis C of the winding core 30. An orientation of the first capillary segment 50 in extension from the first terminal end 52 to the second terminal end 54 serves to define a pitch direction and angle of the first capillary segment 50 relative to the central axis C. Notably, while the first and second terminal ends 52, 54 are circumferentially offset from one another (such that the first capillary segment 50 is characterized as partially spiraling about the cylindrical outer surface 32), partial spiraling of the first capillary segment 50 does not make a full revolution about the central axis C. That is to say, the first capillary segment 50 winds less than 360° about the central axis C in extension from the first terminal end 52 to the second terminal end 54, and thus does not define a complete helix.

Figure 5A:
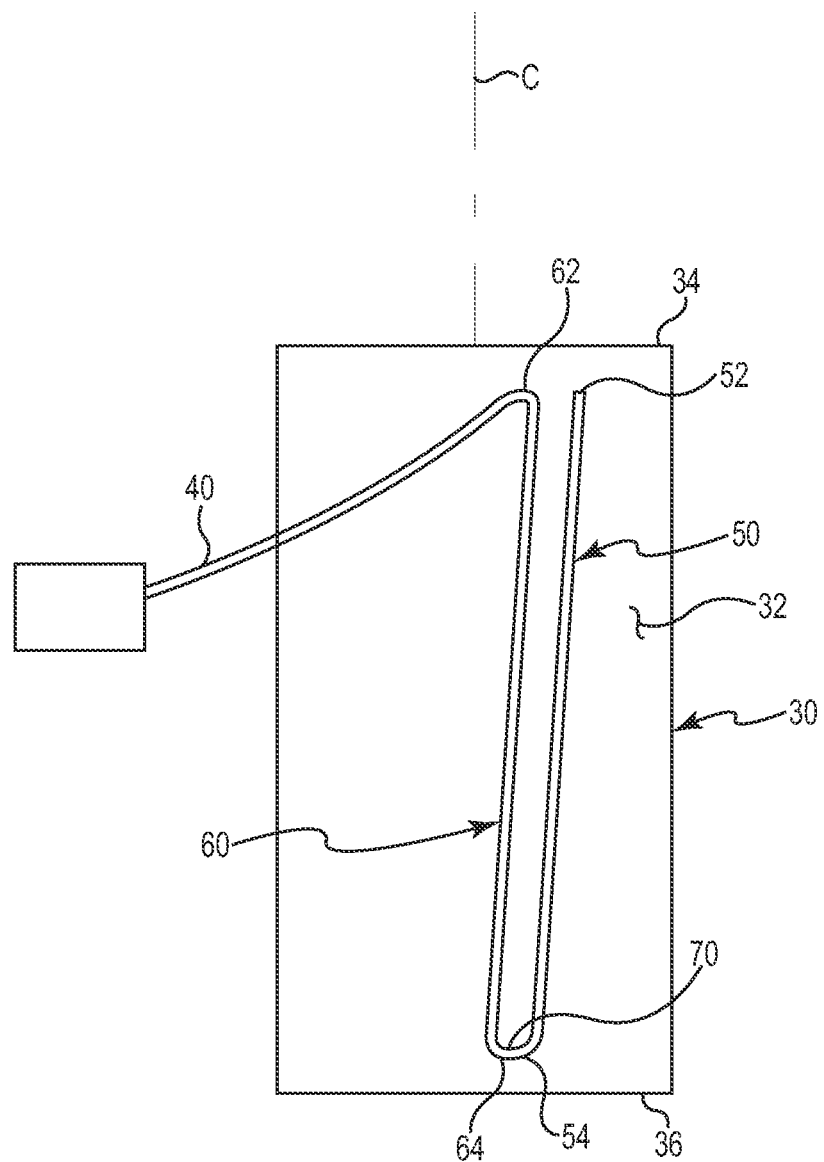
FIG. 5A is a simplified side view illustrating further winding of the capillary tubing, including formation of two capillary segments.

With the second terminal end 54 of the first capillary segment 50 now established relative to the outer surface 32, winding of the capillary tubing 40 continues as shown in FIG. 5A, with the capillary tubing 40 being transversed along the outer surface 32 in an opposite direction, extending from the second terminal end 54 of the first capillary segment 50 toward the first core end 34. At a location generally aligned with the first terminal end 52 of the first capillary segment 50, but circumferentially offset therefrom, the continuous capillary tubing 40 is held (in tension) relative to the outer surface 32 commensurate with previous descriptions. This winding pattern thus establishes a second capillary segment 60 having a first terminal end 62 adjacent the first core end 34, and a second terminal end 64 adjacent the second core end 36. Due to the continuous nature of the capillary tubing 40, the second terminal ends 54, 64 of the first and second capillary segments 50, 60 are commonly formed or shared. Stated otherwise, a turnaround 70 is established in the wound capillary tubing 40, and the segments 50, 60 remain integral or homogenous parts of a continuous capillary tube.

In some embodiments, the circumferential offset (i.e., circumferential arc length) between the first and second terminal ends 52, 54 of the first capillary segment 50 corresponds with the circumferential offset between the first terminal ends 52, 62 of the first and second capillary segments 50, 60. With this construction, then, the second capillary segment 60 is substantially parallel with the first capillary segment 50 (e.g., within 5° of a true parallel relationship). Alternatively, arrangement or orientation of the second capillary segment 60 need not be substantially parallel with the first capillary segment 50. Regardless, extension of the second capillary segment 60 between the corresponding first and second terminal ends 62, 64 is non-parallel relative to the central axis C, and winds about less than 360° of the outer surface 32.

Figure 5B:
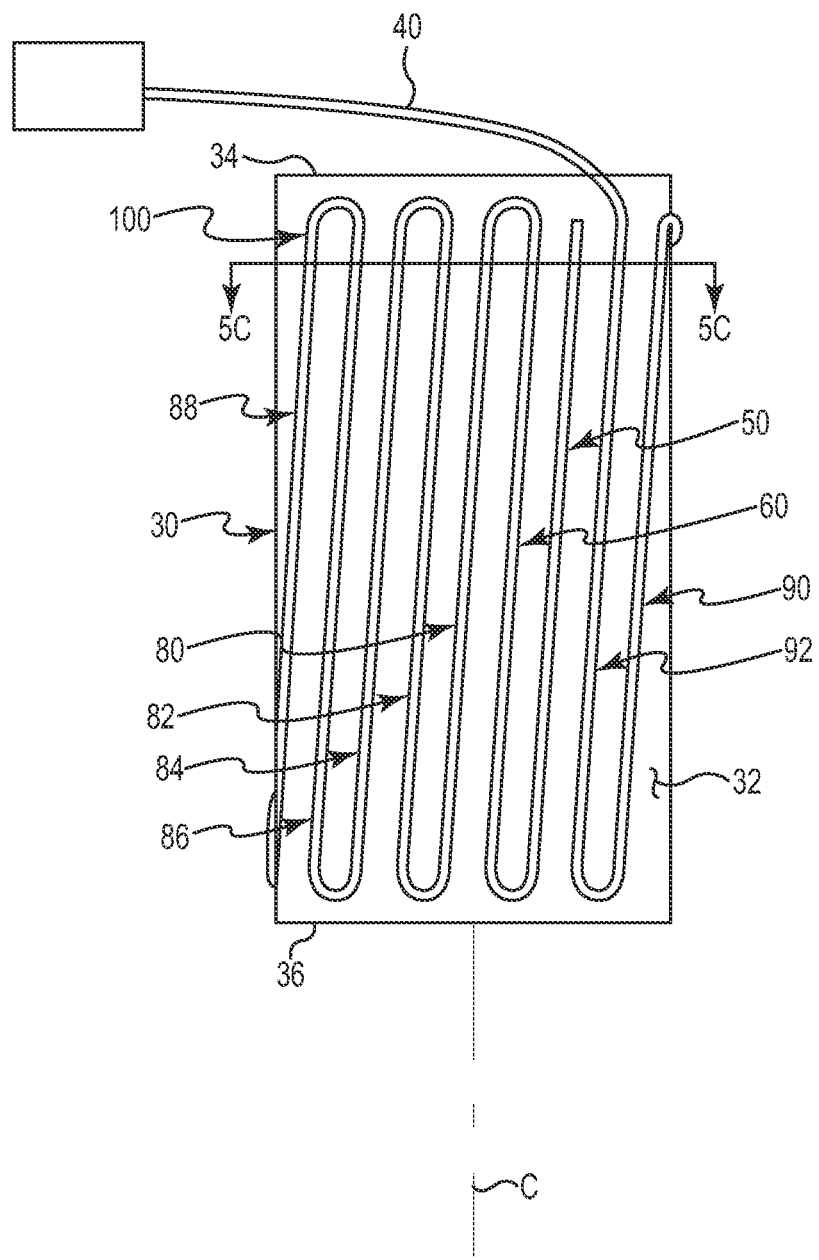
FIG. 5B is a simplified side view illustrating further winding of the capillary tubing, including formation of a first layer.
Figure 5C:
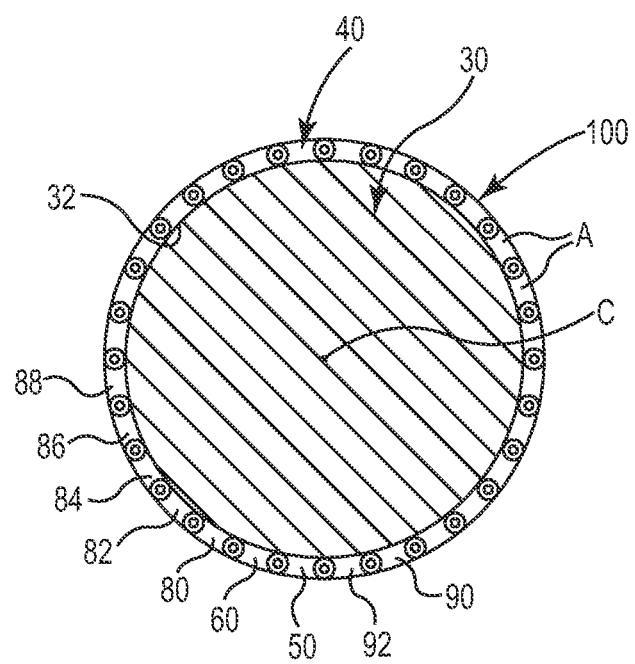
FIG. 5C is a cross-sectional view of the arrangement of FIG. 5B, taken along the line 5C-5C.

Continued tensioned winding of the capillary tubing 40 progresses in a similar fashion, with the capillary tubing 40 being continuously traversed along the cylindrical surface 32, reciprocating between circumferentially offset locations adjacent the first and second core ends 34, 36. As shown in FIG. 5B and 5C, additional capillary segments are thusly formed, each having an orientation in extension between corresponding opposing terminal ends that can be substantially parallel to the first and second capillary segments 50, 60 described above. In the side view of FIG. 5B, the additional capillary segments 80-92 are visible, with the cross-sectional view of FIG. 5C showing all of the capillary segments. At the intermediate stage of winding reflected in FIGS. 5B and 5C, a first layer 100 of capillary segments is generated. As best illustrated in FIG. 5C, the first layer 100 is characterized by each of the corresponding capillary segments commonly designated by "A" in the figures) being substantially concentric about the central axis C or substantially circumferentially aligned with one another relative to the central axis C (e.g., within 5% of a true concentric arrangement or circumfrential alignment). Because the first layer capillary segments A each traverse less than 360° of the outer surface 32, the segments A do not interleave with one another in defining the first layer 100. It will be recalled that two or more continuous capillary tubings 40 can be simultaneously wound and will collectively form the first layer segments A. Regardless, each of the first layer segments A are continuous with another of the first layer segments A, and the terminal ends of each segment A are fluidly closed.

Figure 6A:
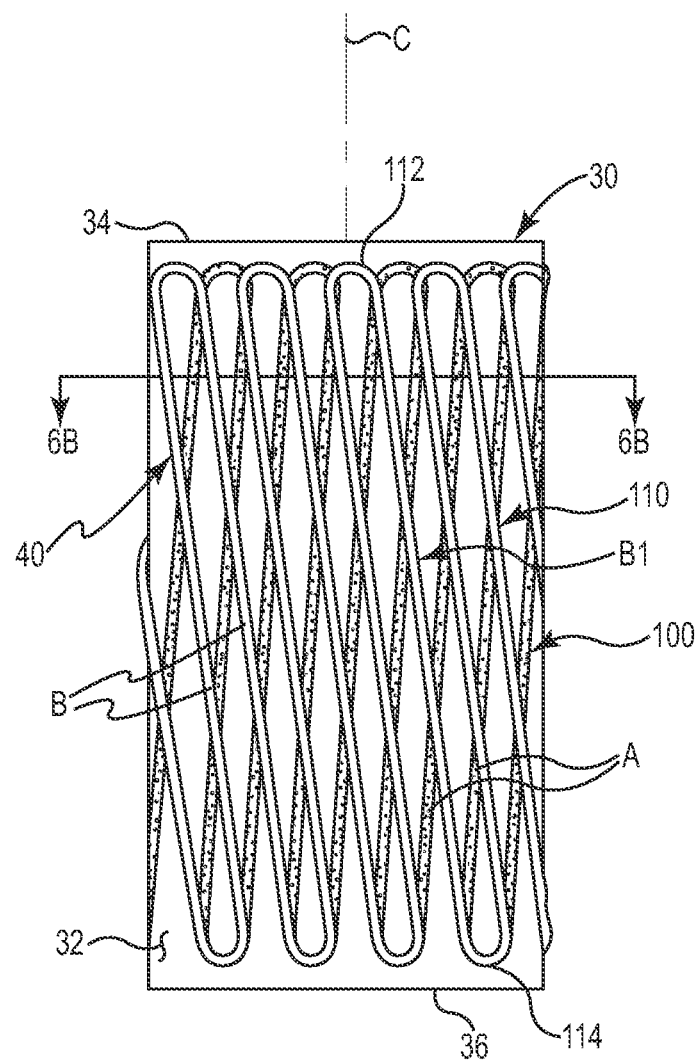
FIG. 6A is a simplified side view illustrating further winding of the capillary tubing, including formation of a second layer over the first layer.
Figure 6B:
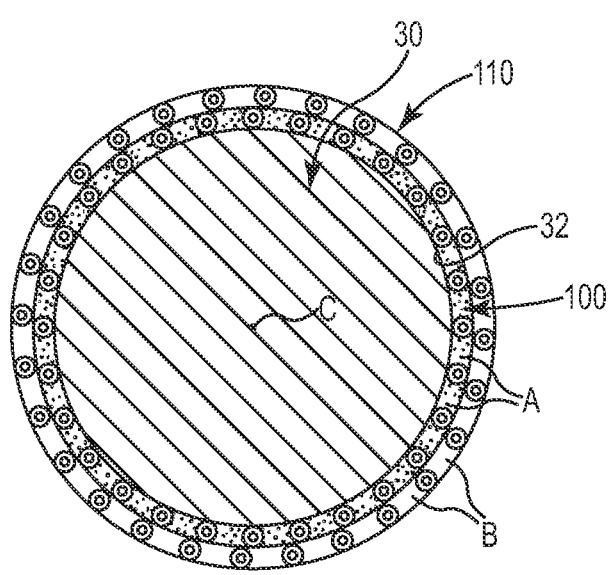
FIG. 6B is a cross-sectional view of the arrangement of FIG. 6A, taken along the line 6B-6B.

Reciprocating winding of the continuous capillary tubing 40 continues further, generating additional capillary layers radially outward of the first layer 100. FIGS. 6A and 6B reflect further tensioned winding of the capillary tubing 40 about the winding core 30 to form a second layer 110. The second layer 110 is radially outward of, but in contact with, the first layer 100. Solely for purposes of explanation, portions of the capillary tubing 40 wound onto the first layer 100 are illustrated with stippling so as to more clearly distinguish the added capillary tubing of the second layer 110 from that of the first layer 100. The second layer 110 is composed of a plurality of capillary segments (generally referenced at "B" in the figures). The second layer capillary segments B are akin to the first layer capillary segments A in that each of the second layer capillary segments B extends between opposing, first and second terminal ends 112, 114 (identified for the second layer capillary segment B1) that are otherwise located adjacent the first and second core ends 34, 36, respectively. Further, the second layer capillary segments B are non-parallel with the central axis C, and partially spiral about the central axis C less than 360° (less than one complete revolution) as described above. However, the orientation of the second layer capillary segments B differs from that of the first layer capillary segments A.

In some embodiments, a pitch direction of the second layer capillary segments B is opposite the pitch direction of the first layer capillary segments A. For example, each of the first layer capillary segments A can be described as having a left hand pitch direction in extension from the corresponding first terminal end to the corresponding second terminal end, whereas the second layer capillary segments B each have a right hand pitch direction in extension from the corresponding first terminal end to the corresponding second terminal end. Alternatively or in addition, an angle of each of the second layer capillary segments B relative to the central axis C is different from the angle defined between the central axis C and each of the first layer capillary segments A. Due to the differing pitch direction and/or angle, the second layer capillary segments B do not nest between the first layer capillary segments A. A purpose of the opposing biases or pitch directions is to prevent any nesting of the capillary segments A, B between the two layers 100, 110, which could result in increased resistance to liquid flow (e.g., blood flow), and undesirable and unpredictable shear on the liquid (e.g., blood) flowing therethrough (i.e., between the capillary segments). Alternatively, the capillary segments A, B can have other angles or biases relative to the central axis C.

Figure 7A:
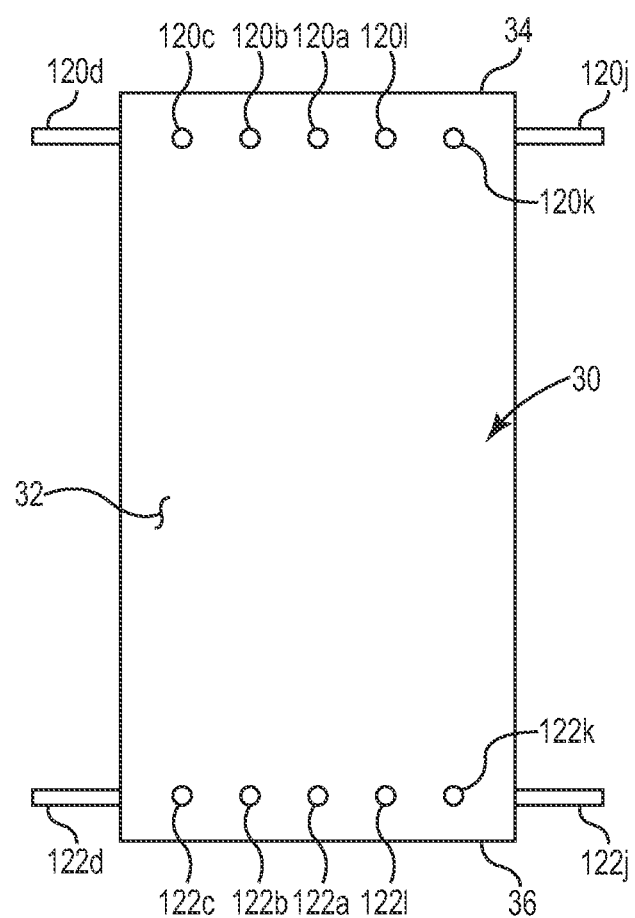
FIG. 7A is a simplified side view of a winding device useful in forming the capillary tubing sub-assembly of the present disclosure including wrapping pins assembled to the winding core of FIG. 3A.
Figure 7B:
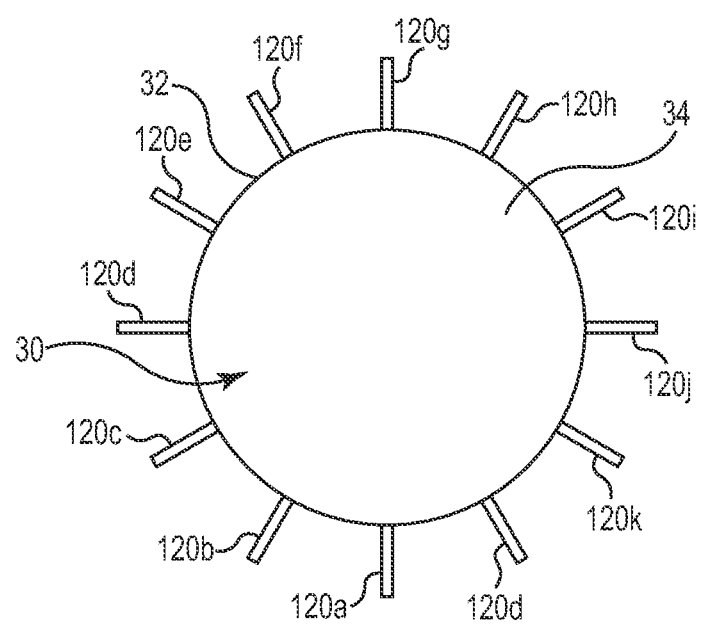
FIG. 7B is an end view of the device of FIG. 7A.

To facilitate a better understanding of the layer-to-layer pitch direction and/or angle differences, it may be helpful to refer to predefined winding turnaround locations established along the core outer surface 32 in accordance with principles of the present disclosure. For example, FIGS. 7A and 7B illustrate, in simplified form, wrapping pins 120, 122 assembled to, and extending outwardly from, the outer surface 32 of the core 30 adjacent the ends 34, 36, respectively. For ease of explanation, relative to the orientation of FIG. 7A, the wrapping pins 120 adjacent the first core end 34 are referred to as "upper" wrapping pins, and the wrapping pins 122 adjacent the second core end 36 are referred to as "lower" wrapping pins, it being understood that the winding core 30 need not be vertically oriented during the winding process. With this in mind, FIGS. 7A and 7B illustrate twelve of the upper wrapping pins 120a-120l and twelve of the lower wrapping pins 122a-122l, although any other number is also acceptable.

Figure 7C:
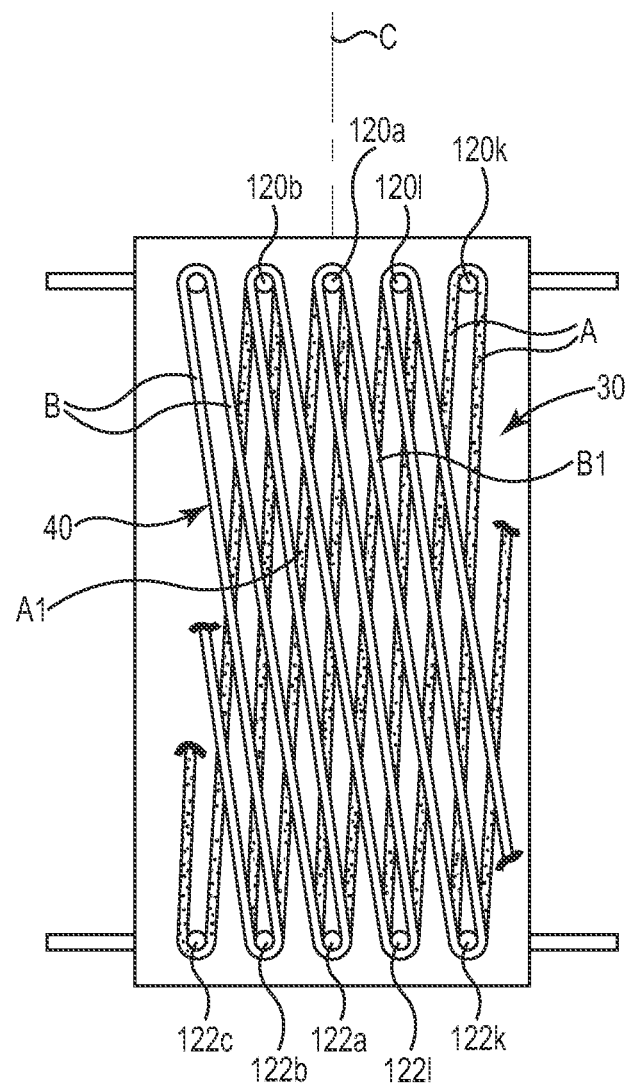
FIG. 7C is a simplified side view of the device of FIG. 7A, and including capillary tubing wound thereto in accordance with principles of the present disclosure.

Respective ones of the wrapping pins 120a-120l, 122a-122l are longitudinally aligned with one another, and the wrapping pins 120a-120l, 122a-122l serve as turnaround locations during winding of the continuous capillary tubing 40 as shown in FIG. 7C. With this in mind, the angle of each of the first layer capillary segments A (relative the central axis C) is dictated by extending the continuous capillary tubing 40 from one of the upper wrapping pins 120a-120l to the circumferentially "next" layer wrapping pin 122a-122l (or vice-versa). For example, with respect to the first layer capillary segment identified at A1 in FIG. 7C, the segment A1 extends from the first upper wrapping pin 120a to the second lower wrapping pin 122b (i.e., relative to the orientation of FIG. 7C, the segment A1 extends in a clockwise direction). The second layer capillary segment identified at B1 not only extends from the first upper wrapping pin 120a in a counterclockwise direction, but terminates at the eleventh lower wrapping pin 122k. By effectively "skipping" the twelfth lower wrapping pin 122*l*, the second layer capillary segment B1 is oriented at an angle differing from that of the first layer capillary segment A1. Winding of the continuous capillary tubing 40 in forming the second layer 110 (FIG. 6B) follows this same pattern, dictating that all of the second layer capillary segments B are oriented differently from the first layer capillary segments A.

Winding of the continuous capillary tubing 40 continues further in a similar fashion, generating additional, radially outward layers, each consisting of a plurality of capillary segments that are substantially circumferentially aligned relative to the central axis C, non-parallel with the central axis C, and partially spiraled about the central axis C by less than 360°. An orientation (e.g., pitch direction, angle, etc.) of the capillary segments differ from layer-to-layer to impede inter-layer nesting as described above. Other variables can be introduced during the winding process. For example, in addition or as an alternative to varying the pitch direction or angle, the number of capillary segments within a particular layer can be varied. The capillary tubing itself can be varied from one layer to the next, for example by employing capillary tubing having a different inner and/or outer diameter with different ones of the capillary layers. These variations, in turn, can effectuate a desired packing fraction in the resultant capillary tube bundle 20 (FIG. 1A). For purposes of this disclosure, packing fraction is defined to mean the fraction of a unit volume of bundle space occupied by capillary tubing segments. The packing fraction can be determined in ways known in the art, including the conventional method of measuring the interstitial space between the capillary segments by weight gain when a unit volume is primed with a known liquid. Packing fraction in a particular region or zone located radially outward may be determined by stopping the corresponding winding process at the radially inner radial boundary of the region or zone and determining the zone at that stage, and then continuing the winding process to the outer radial boundary of the region or zone in determining the zone or fraction at that stage. Computations known in the art will determine the packaging fraction of the region or zone using the prior to values.

Figure 8A:
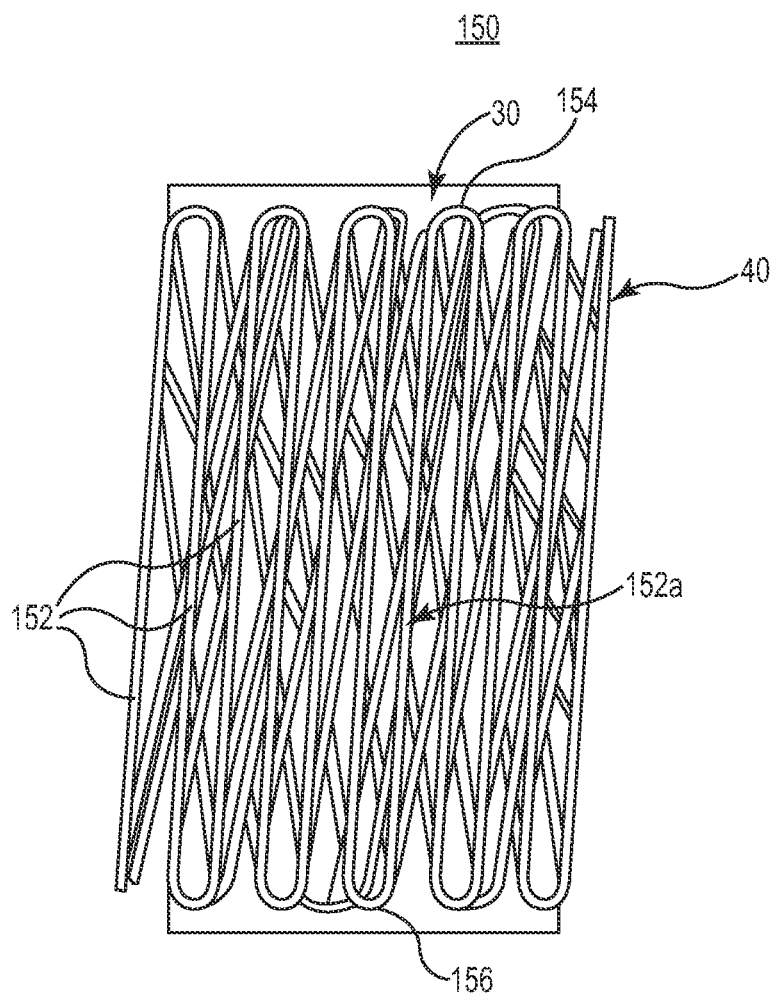
FIG. 8A is a simplified side view of a capillary tube bundle sub-assembly in accordance with principles of the present disclosure.
Figure 8B:
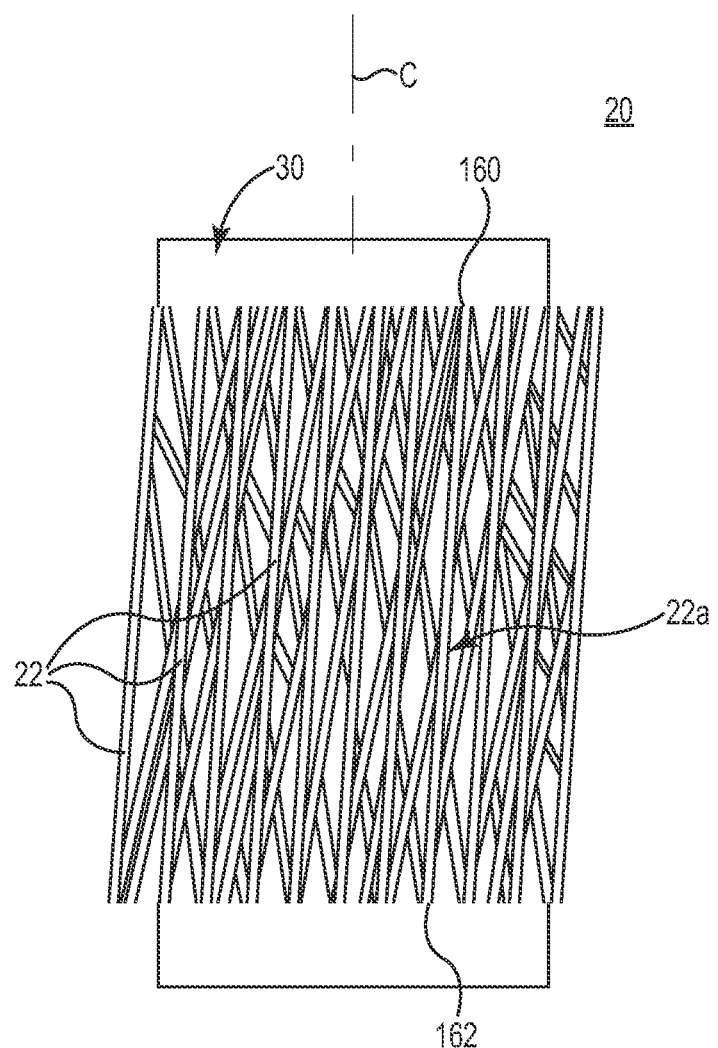
FIG. 8B is a simplified side view of a capillary tube bundle produced from the capillary tube bundle sub-assembly of FIG. 8A.

Once a desired number of capillary layers have been wound to the winding core 30, the winding process is complete, resulting in a capillary tube bundle sub-assembly 150 is illustrated in FIG. 8A. The number of layers provided with the final capillary tube bundle sub-assembly 150 can be selected in accordance with a desired end performance. In the sub-assembly form, the continuous capillary tubing 40 is still continuous such that none of the capillary segments (referenced generally at 152) are exteriorly open (other than, perhaps, at the opposing ends of the continuous capillary tubing 40). To facilitate use as part of a heat exchanger, the capillary segments 152 each must then be opened at the corresponding opposing terminal ends, for example via a cutting procedure. For example, the optional bands 26 (FIG. 1A) are applied to the wound capillary tubing 40 so as to maintain the tension in the capillary segments 152. The capillary segments 152 are then cut (e.g., a conventional hot knife) at locations proximate the opposing terminal ends 154, 156 (identified for one of the capillary segments 152*a* in FIG. 8A). The fluidly closed or continuous terminal ends 154, 156 of each of the capillary segments 152 are thus removed or otherwise opened relative to the capillary lumen, resulting in the discrete capillary tubes 22 identified generally in FIG. 8B, with each capillary tube 22 extending between opposing, first and second open ends 160, 162 (identified for one of the capillary tubes 22*a* in FIG. 8B). Optionally, the ends 160, 162 can be embedded in a solidified potting compound as known to those of ordinary skill. Stated otherwise, the cutting process (and optional potting process) transitions the capillary tube bundle sub-assembly 150 of FIG. 8A to the capillary tube bundle 20 of FIG. 8B. The capillary tubes 22 are essentially identical to the capillary segments 152 (FIG. 8A) described above, except that the continuous terminal ends no longer exist. The capillary tubes 22 form the plurality of concentric layers previously described, and each extend non-parallel with the central axis C and partially spiral (less than 360°) about the central axis C. Notably, the capillary tube bundle 20 does not include threads or stitching interconnecting the capillary tubes 22 as otherwise found with conventional mat-based heat exchanger bundles. Further, commensurate with the above descriptions, a variable packing fraction or other variations can be incorporated into the bundle 20. The capillary tube bundle 20 can then be assembled with other components to form a heat exchanger.

While the above-described methods of forming the capillary tube bundle sub-assembly 150 includes winding the capillary tubing about wrapping pins embedded into the winding core 30, other techniques are also contemplated. For example, continuous winding equipment can be used, including a fiber guide that moves the capillary tubing 40 (FIG. 5B), or a ribbon of capillary tubings 40, in a reciprocating fashion relative to the winding core 30, along with a rotational mounting member that rotates the winding core 30 relative to the fiber guide. With this construction, the winding core 30 is continuously rotated with reciprocating movement of the fiber guide, but rotates less than 360° during each traversing movement of the fiber guide. In other embodiments, the winding core 30 can be elongated. During subsequent cutting operations, the sub-assembly 150 (FIG. 8A) is severed at one or more intermediate locations to create two (or more) capillary tube bundles 20 from a single sub-assembly 150. In related embodiments, the segments 152 of the elongated sub-assembly 150 can traverse more than 360°, with the final capillary tube bundles 20 being cut at longitudinal locations where the resultant tubes 22 wrap less than 360°.

In some constructions, the winding core 30 about which the capillary tubing 40 (FIG. 5B) is wound is configured for assembly and use within a radial flow-type heat exchanger apparatus. In other embodiments, the capillary tube bundle sub-assembly 150 (or the capillary tube bundle 20) can be removed from the winding core 30 and assembled over a separate core specifically designed for a particular heat exchanger. As shown in FIG. 1B, then, the heat exchanger core 24 can assume a variety of forms, and generally defines an inlet 200, a central passageway 202, and one or more outlet openings 204. The inlet 200 is fluidly open to the passageway 202, as are the outlet openings 204. With embodiments in which the resultant heat exchanger apparatus is intended to impart a radially outward flow pattern onto liquid flowing through the passageway 202 (and otherwise entering the passageway 202 via the inlet 200), the openings 204 can be formed along an inner portion of the core 24, projecting through a wall thickness thereof. Other locations for the outlet opening(s) 204 are equally acceptable. As a point of reference, the term "heat exchanger" is a component including the capillary tube bundle 20 and the heat exchanger core 24. The so-defined heat exchanger can be utilized as part of a standalone, finished heat exchanger apparatus or device that otherwise includes an outer housing and various fluid ports. Alternatively, the so-defined heat exchanger can serve as a subassembly component of a combination extracorporeal blood circuit apparatus or device that performs heat exchange and one or more additional functions.

Figure 9:
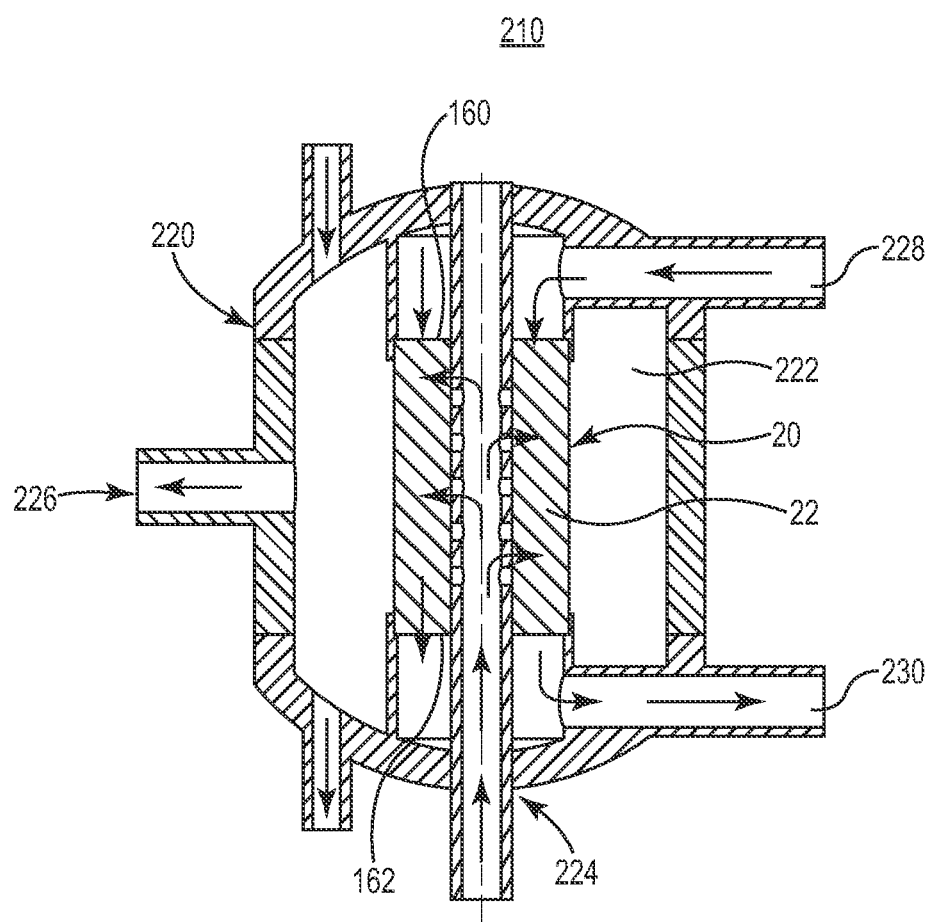
FIG. 9 is a simplified cross-sectional view of a heat exchanger apparatus in accordance with principles of the present disclosure, including the capillary tube bundle of FIG. 1A.

One example of a heat exchanger apparatus 210 is constructed with the capillary tube bundle 20 by assembling the bundle 20 within a housing 220 as generally reflected in FIG. 9. The housing 220 can assume various forms, and generally includes or defines a chamber 222 sized to receive the capillary tube bundle 20, a blood inlet 224, a blood outlet 226, a heat exchange inlet 228, and a heat exchange outlet 230. With embodiments in which the heat exchanger apparatus 210 functions by forcing heat exchange fluid through the lumens of the capillary tubes 22 (drawn schematically), the blood inlet 224 is fluidly connected to the central passageway 202 of the core 24. The blood outlet 226 is fluidly connected the chamber 222 radially opposite the capillary tube bundle 20. The heat exchange inlet 228 is fluidly connected to the first open ends (or inflow ends) 160 of the capillary tubes 22, whereas the heat exchange outlet 230 is fluidly connected to the second open ends for outflow ends) 162 of the capillary tubes 22.

Figure 10:
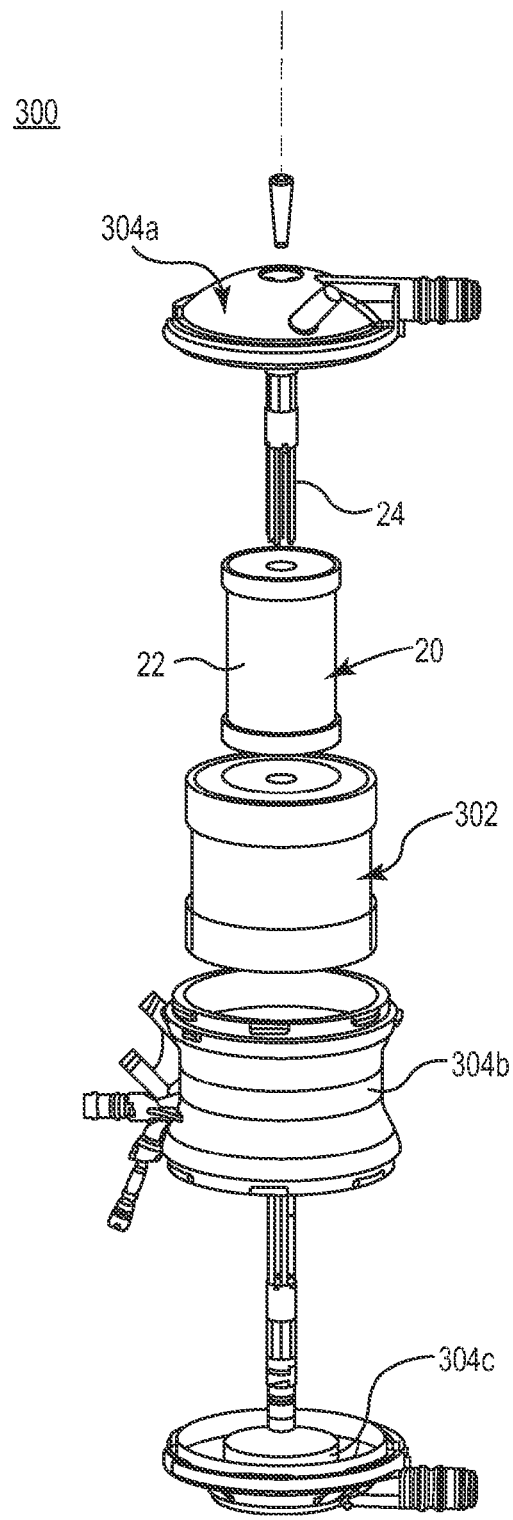
FIG. 10 is an exploded, perspective view of an extracorporeal circuit apparatus in accordance with principles of the present disclosure, including the capillary tube bundle of FIG. 1A.

When the heat exchanger apparatus 210 is assembled as part of an extracorporeal blood circuit, blood flow from the patient is introduced at the blood inlet 224. Heat exchange liquid is introduced at the heat exchange inlet 228. The heat exchanger apparatus 210 may either heat or cool the blood flowing through the heat exchanger apparatus 210. Since hypothermia may be caused during cardiac surgery (especially in infant and pediatric surgeries) to reduce oxygen demand, and since rapid re-warming of the blood undesirably produces bubble emboli, the heat exchanger 210 is generally used to gradually re-warm blood and prevent emboli formation. The heat transfer medium used in the heat exchanger apparatus 210 can comprise water or other suitable fluids. FIG. 9 includes arrows (labeled as "fluid) that shows the flow of a heat exchange medium through the heat exchanger apparatus 210, and in particular the capillary tubes 22, with entry at the heat exchange inlet 228 and exit at the heat exchange outlet 230. After flowing through the core passageway 202, blood moves sequentially radially outwardly through the capillary tubes 22. The direction of blood flow is directed by arrows (labeled as "blood"), In yet other embodiments, the capillary tube bundle 20 (and core 24) can be a heat exchanger incorporated into or as part of other fluid handling apparatuses or devices performing functions in addition to heat exchange. For example, FIG. 10 illustrates a combination oxygenator and heat exchanger apparatus 300 incorporating the capillary tube bundle 20 described above. The apparatus 300 further includes an oxygenator 302 and various housing components (referenced generally at 304a-304c). The oxygenator 302 can assume any form known in the art, as can the housing components 304a-304c. For ease of illustration, FIG. 10 illustrates the core 24 apart from the capillary tubes 22 (referenced generally). In other embodiments, the apparatus 300 can include a separate supportive core over which the heat exchanger core 24 is disposed.

Figure 11:
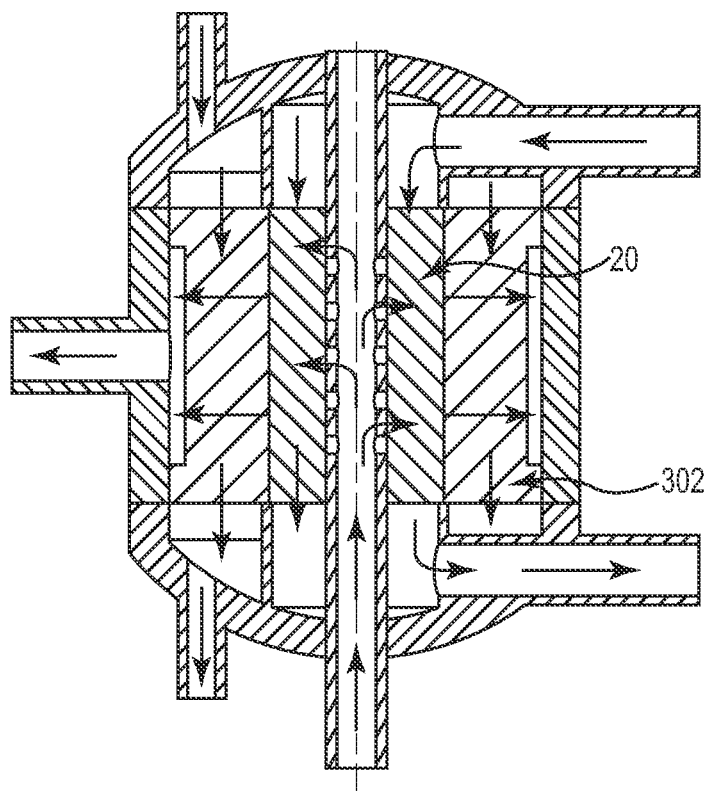
FIG. 11 is a simplified, cross-sectional view of the apparatus of FIG. 10.

FIG. 11 shows, in simplified form, fluid flow through the apparatus 300. A heat transfer medium flows through the heat exchanger capillary tube bundle 20 as shown by the arrows "fluid". After flowing through the heat exchanger capillary tube bundle 20, blood moves sequentially and radially outwardly and through the oxygenator 302 that is otherwise arranged around the heat exchanger capillary tube bundle 20. The direction of blood flow is indicated by arrows labeled as "blood". FIG. 11 also includes arrows that show the flow of an oxygen-containing medium through the oxygenator 302 (labeled as "gas"). The oxygenator 302 may concentrically surround the heat exchanger capillary tube bundle 20 (e.g., as one or more continuous micro porous fibers). It will be understood that the heat exchanger capillary bundle 20 of the present disclosure can be incorporated into a plethora of other apparatuses that may or may not include the oxygenator 302.

The capillary tube bundles, capillary tube bundle sub-assemblies, and methods of manufacturing thereof, of the present disclosure provide marked improvements over existing devices and methods. By allowing heat exchanger manufactures to select one or more characteristics of the wound capillary tube(s) during winding, heat exchanger capillary bundles of the present disclosure exhibit reduced costs, controlled packing fraction, and optionally variable capillary diameters.

Although the present disclosure has been described with reference to preferred embodiments, workers skilled in the art will recognize that changes can be made in form and detail without departing from the spirit and scope of the present disclosure.

What is claimed is:

1. An extracorporeal blood circuit apparatus for performing heat exchange comprising:
 a housing defining:
 a blood flow path from a blood inlet to a blood outlet, and
 a heat exchange fluid pathway from a heat exchange inlet to a heat exchange outlet;
 a capillary tube bundle disposed within the housing and including:
 a core defining a cylindrical outer surface having a central axis, a first core end, a second core end opposite the first core end, and a length between the core ends in a direction of the central axis,
 a plurality of fluid impermeable capillary tubes disposed about the outer surface to define a plurality of capillary layers, wherein:
 the capillary tubes of each layer are substantially circumferentially aligned relative to the central axis and each successive layer is radially outward of an immediately preceding layer,
 each of the capillary tubes is non-parallel with the central axis, traversing a majority of the core length from a first open end adjacent the first core end to a second open end adjacent the second core end,
 each of the capillary tubes spirals partially about the central axis in extension from the corresponding first open end to the corresponding second open end by less than 360°, and
 an orientation of the capillary tubes in a first one of the layers differs from an orientation of the capillary tubes in a second one of the layers;
 a first band disposed about the first open end of each of the capillary tubes, the first open ends being fluidly open to one of the blood inlet and the heat exchange inlet; and
 a second band disposed about the second open end of each of the capillary tubes, the second open ends being fluidly open to one of the blood outlet and the heat exchange outlet.

2. The apparatus of claim 1, wherein the second layer is disposed against the first layer opposite the outer surface.

3. The apparatus of claim 2, wherein the capillary tubes of the first layer have a pitch direction in extension from the corresponding first open end to the corresponding second open end, and the capillary tubes of the second layer have a second pitch direction in extension from the corresponding first open end to the corresponding second open end, the first pitch direction being opposite the second pitch direction.

4. The apparatus of claim 3, wherein the capillary tubes of the first layer are arranged at a right hand pitch and the capillary tubes of the second layer are arranged at a left hand pitch.

5. The apparatus of claim 2, wherein the capillary tubes of the first layer are substantially parallel with one another in extension from the corresponding first open end to the corresponding second open end.

6. The apparatus of claim 2, wherein each of the capillary tubes of the first layer are arranged at a first angle relative to the central axis and each of the capillary tubes of the second layer are arranged at a second angle relative to the central axis, the first angle being different from the second angle.

7. The apparatus of claim 1, wherein the capillary tube bundle is characterized by the absence of a thread interconnecting each of the capillary tubes of the first layer.

8. The apparatus of claim 1, wherein the core forms a central passageway and radial openings from the central passageway to the outer surface, the central passageway being fluidly connected to the blood inlet to establish a radial flow of blood through the layers.

9. The apparatus of claim 8, wherein the first open ends are fluidly connected to the heat exchange inlet and the second open ends are fluidly connected to the heat exchange outlet, and further wherein when connected to an extracorporeal blood circuit, the heat exchanger is configured to direct blood flow from the blood inlet and radially between the plurality of capillary tubes, and further to direct heat exchange fluid through a lumen of each of the capillary tubes.

10. A method of making a capillary tube bundle for use in a heat exchanger of an extracorporeal blood circuit apparatus, the method comprising:
   guiding a continuous capillary tube in a first direction along an outer cylindrical surface of a core substrate to form a first capillary segment extending from a first terminal end adjacent a first core end of the core to a second terminal end adjacent an opposing, second core end of the core, wherein the first terminal end is circumferentially offset from the second terminal end such that an entirety of the first capillary segment is non-parallel with a central axis of the core, and the first capillary segment traverses less than 360° of the outer surface;
   guiding the continuous capillary tubing in a second direction opposite the first direction to form a second capillary segment immediately adjacent the first capillary segment, the second capillary segment including opposing, first and second terminal ends, wherein the first and second capillary segments combine to form a portion of a first layer of capillary segments substantially circumferentially aligned about the central axis; and
   guiding the continuous capillary tubing in a reciprocating fashion relative to the core to form a second layer of fiber segments radially outward of the first layer.

11. The method of claim 10, wherein the capillary tubing continuously forms second terminal ends of the first and second capillary segments at a turnaround point.

12. The method of claim 10, wherein the first and second capillary segments are substantially parallel.

13. The method of claim 10, wherein the capillary segments of the first layer extend in a first pitch direction, and the capillary segments of the second layer extend in a second pitch direction opposite the first pitch direction.

14. The method of claim 10, wherein a circumferential offset of the first and second terminal ends of each of the capillary segments of the first layer differs from a circumferential offset of the first and second terminal ends of each of the capillary segments of the second layer.

15. The method of claim 10, wherein the steps of guiding the continuous capillary tubing include:
   reciprocating a fiber guide relative to the core; and
   rotating the core simultaneously with reciprocating movement of the fiber guide, wherein the core is rotated less than 360° during each traversing movement of the fiber guide.

16. The method of claim 10, further comprising:
   cutting each of the capillary segments adjacent the corresponding first and second terminal ends to fluidly open each of the capillary segments and form a plurality of discrete capillary tubes.

17. The method of claim 10, wherein the capillary tubes are liquid impermeable.

* * * * *